United States Patent [19]

Rasch et al.

[11] 4,259,164
[45] Mar. 31, 1981

[54] SILVER/SILVER HALIDE ELECTRODES COMPRISING CHROMIUM OR NICKEL

[75] Inventors: Arthur A. Rasch; Roger Searle, both of Rochester, N.Y.

[73] Assignee: Eastman Kodak Company, Rochester, N.Y.

[21] Appl. No.: 66,123

[22] Filed: Aug. 13, 1979

[51] Int. Cl.³ ............................................. G01N 27/26
[52] U.S. Cl. ............................ 204/195 F; 204/195 M; 204/195 P
[58] Field of Search ........... 204/195 R, 195 F, 195 H, 204/195 M, 195 P

[56] References Cited

U.S. PATENT DOCUMENTS

| | | | |
|---|---|---|---|
| 3,562,129 | 8/1967 | Simon | 204/195 M |
| 3,753,887 | 8/1973 | Kedem et al. | 204/195 M |
| 3,856,649 | 12/1974 | Genshaw et al. | 204/195 F |

FOREIGN PATENT DOCUMENTS 1375446  11/1974  United Kingdom .

OTHER PUBLICATIONS

Research Disclosure 16113, vol. 161, Sep. 1977, pp. 29–39.

Primary Examiner—Ralph S. Kendall
Assistant Examiner—Richard Bueker
Attorney, Agent, or Firm—Arthur H. Rosenstein

[57] ABSTRACT

A silver/silver halide electrode is prepared by coating portions of a layer of silver with a metal selected from the group consisting of chromium and nickel or mixtures or alloys of nickel and chromium and overall treating with an oxidizing agent in the presence of halide ions to form a silver halide layer on those portions of the silver layer not covered by metal. The electrodes can be used as assaying electrodes such as for halide ions or as reference electrodes. Reference elements formed from the reference electrodes are useful in providing ion-selective membrane electrodes.

18 Claims, 2 Drawing Figures

SILVER/SILVER HALIDE ELECTRODES COMPRISING CHROMIUM OR NICKEL

This application relates to a process for preparing silver/silver halide electrodes, reference electrodes, reference elements and ion-selective membrane electrodes and the electrodes, reference elements and ion-selective membrane electrodes prepared thereby.

The use of electrodes for the measurement of various ionic solutions is widespread. Typically, devices for obtaining such measurements include either a metal/metal halide electrode useful for the measurement of halide ion such as Cl and Br or a reference element comprising a reference electrode and a separate ion-selective electrode. When simultaneously contacted with the solution to be analyzed, the reference and ion-selective electrodes constitute an electrochemical cell, across which a potential develops. Measurement of the potential determines the concentration of ions in the solution.

The electrode or reference electrode may comprise silver coated with silver halide and the reference element contains the reference electrode overcoated with a layer comprising a metal salt electrolyte.

One useful reference element for ion-selective electrodes comprises a metal in contact with an insoluble salt of the metal which is in turn in contact with an electrolyte, i.e., a solution containing the anion of the salt. A very commonly used example of such a reference element can be represented as Ag-/AgCl/"XMCl−" (XMCl− indicating a solution of known Cl− concentration) and comprises a silver wire having a coating of silver chloride dipped into an aqueous solution of known chloride concentration.

The silver halide layer of the electrode or reference electrode is conventionally coated on the silver substrate by contacting the silver substrate with an oxidizing agent and drying. In the case of the reference electrode, this is done prior to overcoating with an electrolyte layer.

In copending U.S. Application Ser. No. 893,656 of Battaglia et al, a reference element is described which is formed by coating a support such as poly(ethylene terephthalate) with a metallic silver layer, such as by plating techniques, and treating the silver layer overall with an oxidizing agent or a silver halide emulsion and drying. The surface of the silver layer is thus converted to or coated by silver halide. The layer is dried and the silver halide layer is overcoated with an electrolyte layer comprising the metal salt forming the electrolyte and a hydrophilc binder. The resulting reference element is a substrate overall coated with a silver layer, overall coated with a silver halide layer and overall coated with the electrolyte layer. A membrane layer is added and the resulting ion-selective electrode is completed by connecting a probe by penetrating through the silver halide layer to the silver layer for electrical contact.

Although the above method results in an acceptable reference element, the electrical contact of the probe with the silver layer is not always good, as the probe must be forced through the silver halide layer to make contact with the silver layer.

SUMMARY OF THE INVENTION

According to the present invention, there is provided a novel method for preparing a silver/silver halide electrode comprising coating portions of a silver layer with a metal of the group consisting of nickel and chromium and overall treating with an oxidizing agent.

This process protects the silver areas under the metal from undesirable oxidation while forming the silver halide layer in uncovered areas. Electrical contact can therefore be made directly with the metal coating without interference from the silver halide layer.

According to a further embodiment of the present invention, a reference element can be formed by further coating the silver halide electrode with a layer containing a metal salt electrolyte.

In a still further embodiment of the present invention, an ion-selective electrode is prepared by coating portions of a silver layer with a metal selected from the group consisting of chromium and nickel and mixtures or alloys of chromium and nickel and overall treating with a composition comprising an oxidizing agent and a metal salt electrolyte and overcoating the resulting reference element with a hydrophobic membrane layer containing an ionophore and an ion-carrier solvent and a hydrophobic binder. The membrane layer is useful in electrodes which measure ions, such as potassium, carbonate and the like.

In another embodiment of the present invention, a halide ion-sensitive electrode is prepared by preparing the silver/silver halide electrode as described above and overcoating with a polymeric layer to reduce interference from other halide ions and uric acid.

DESCRIPTION OF THE PREFERRED EMBODIMENTS

Figure 1:
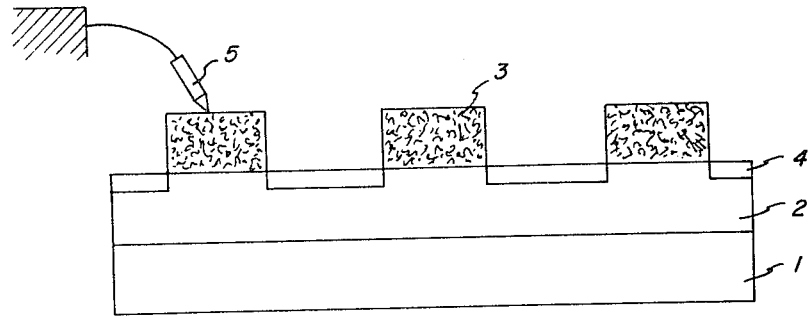
FIG. 1 of the drawings shows a cross-sectional view of an electrode or reference electrode as described herein.

The electrodes of the present invention are prepared by coating portions of a silver layer with a metal selected from the group consisting of chromium and nickel and mixtures and alloys of chromium and nickel and overall treating with an oxidizing agent.

The silver layer can either be self-supported or coated on a support. Suitable supports for a silver layer are preferably insulating and include glass, paper and polymeric supports, such as polyesters such as poly-(ethylene terephthalate), cellulose ester materials and the like.

The silver layer can be formed in situ or coated onto a support using any suitable method of depositing silver. The silver layer, preferably a thin layer, can be formed by electroless deposition, vapor deposition of silver in vacuum, depositing a photographic silver halide layer and exposing and developing to form silver and the like.

Portions of the silver layer are then coated with the metal selected from the group consisting of chromium and nickel and mixtures or alloys of chromium and nickel.

The metal can be coated onto the silver layer using any conventional coating technique. The coating is applied, however, to only a portion of the silver layer, leaving the remainder of the layer uncoated. In a preferred embodiment, the metal is applied in stripes to the silver layer by the process of vapor deposition in vacuum. The desired pattern is formed by placing a mask between the vapor source and the silver film, using methods well known in the art, so that only clearly delineated areas are coated with the protective chromium or nickel film.

The use of chromium or nickel as protective films on the silver layer prevents the underlying silve from reacting with the oxidizing agent to form silver halide. These metals are good electrical conductors and react very slowly, if at all, with the oxidizing agents. As a result, direct electrical contact can be made to the underlying silver film without the necessity of first mechanically penetrating an electrically resistive silver halide film. In this way, the reliability of the electrode made from this method is improved.

By "coating portions of a silver layer" it is meant that the silver layer would, in some areas, be coated and in other areas be uncoated. The most preferable method of partially coating the silver layer is to coat in a striped fashion. That is, the coating is applied in individual striped areas leaving the remainder of the silver layer uncoated.

The chromium or nickel films can be very thin. For example, films 50 Å thick are found to prevent reaction of the silver with the oxidizing agent.

The nickel and chromium protective films not only provide good electrical contact and protect the underlying silver from the oxidizing agent, but they do not appreciably accelerate the reaction of immediately adjacent unprotected silver with the oxidizing agent. Thin films of other metals either fail to protect the underlying silver from the oxidizing agent or fail to provide good electrical contact or the silver layers in the areas adjacent to the protective metal even as far as 2 mm away, react more rapidly than the remainder of the silver layer. Reaction rates at these areas can accelerate more than two fold with the result that the silver in these areas is etched through and electrical continuity in the silver films is lost.

The partially chromium or nickel coated silver is then overall coated or treated with a composition comprising an oxidizing agent (and halide ions if said oxidizing agent does not contain same) which produces the silver halide layer on the unprotected silver. The oxidizing agent can be applied to the silver using any conventional techniques such as roll coating, dipping, laminating, brush coating or other coating techniques. The oxidizing agent can be in a solution such as an acid solution, such as hydrochloric acid and the like containing the oxidizing agent.

Examples of useful oxidizing agents are $K(CrO_3Cl)$, $K_3Fe(CN)_6$, $KMnO_4$, $K_2Cr_2O_7$, $NH_4VO_3$, $(NH_4)_2Ce(NO_3)_6$, $Fe(C_2O_4)_3$ and the like. Preferred oxidizing agents are $K(CrO_3Cl)$ and $K_3Fe(CN)_6$. Combinations of oxidizing agents can be used. A more thorough listing of oxidizing agents useful herein can be found in *Handbook of Chemistry and Physics*, 50th Edition, The Chemical Rubber Company, 1969, pp D109-114.

The amount of oxidizing agent used can vary depending on its oxidizing power, but preferably the coverage should be between 0.01 and 2.0 $g/m^2$.

Thus, as seen in FIG. 1, a typical manufacturing procedure for an electrode will involve applying in striped fashion layers of chromium or nickel 3 or mixtures or alloys thereof to a layer of silver 2 vacuum-deposited on a poly(ethylene terephthalate) support 1 and treating with the oxidizing agent so as to form silver halide layers 4 in only those unprotected areas of the silver layer and making an ohmic contact with the underlying silver layer with probe 5 by connecting to the chromium or nickel layers.

A reference element can be obtained by coating only the silver halide areas with a composition comprising a metal salt electrolyte. The coating composition can contain the metal salt and hydrophilic binder.

The coating composition can comprise a metal salt electrolyte mixed with a hydrophilic binder. In a preferred embodiment, one of the ions of said salt comprises the ion which the electrode is designed to detect. Typically, the binder and salt are in solution with a solvent for both.

The binder for the electrolyte solution may comprise any hydrophilic material suitable for the formation of continuous, coherent, cohesive layers compatible with the salt of the electrolyte layer and, if formed by coating, a solvent for both the ionic salt and the polymeric binder. Preferred materials of this type are hydrophilic, natural and synthetic polymeric film-forming materials, such as polyvinyl alcohol, gelatin, agarose, polyacrylamide, polyvinyl pyrrolidone, hydroxyethyl acrylate, hydroxyethyl methacrylate, polyacrylic acid, etc. Specifically preferred from among these materials are the hydrophilic colloids, such as gelatin (especially deionized gelatin), agarose, polyvinyl alcohol and hydroxyethyl acrylate.

The ionic salt which is dissolved in the polymeric binder solution will be determined by the ion to be detected. For example, in a potassium-selective electrode which uses AgCl as the insoluble metal salt, potassium chloride is a logical choice, although sodium chloride, etc., may also be used. For sodium ion determinations in a similar confirguration, sodium chloride would be useful, etc. Thus, the salt will generally be a water-soluble salt having a cation selected from ammonium, alkali metals and alkaline earth metals, mixtures of the same, and as the anion, a halogen, carbonate or sulfur or any other suitable ion to which the electrode responds, depending upon the composition of the metal-salt layer.

In the case of a silver/silver halide electrode to be used directly to determine ions such as Cl and Br, no electrolyte layer is needed. In the case of an ion-selective membrane electrode for determining $K^+$, $CO_3^=$ and the like, the composition to be coated over the silver chloride layer can generally comprise from about 0.1 to about 7.5 $g/m^2$ of metal salt and from about 0.5 to about 10 $g/m^2$ of hydrophilic binder. Generally, salt concentrations of from about 30% to about 50% by weight of the binders in the layer are preferred.

The coating composition can also contain other addenda, such as surfactants, for example saponin, (p-isononyl phenoxy polyglycidol), Surfactant 10 G (a nonionic surfactant made by the Olin Corporation) and the like; buffering agents, such as phosphates, acetic acid and the like.

Appropriate solvents for the polymeric binder and ionic salt will depend largely on the nature of the polymer and the salt. Generally, polar solvents suitable for dissolving the salt and the polymer are satisfactory. Thus, water is a preferred solvent for layers of hydrophilic materials, such as polyvinyl alcohol and gelatin.

Since the thickness of the metal salt layer will, to some extent, determine the response characteristics of the electrode, it is generally desirable to keep the layer rather thin. Layers having thicknesses on the order of from about 0.1 to about 0.5 mil have been found useful. A preferred thickness is about 0.2 mil. Of course, where electrode response characteristics are not critical, the thickness of the layer may vary over a wide range. The application of sound engineering skills and the use requirements of the finished electrode will determine its limits The electrodes can comprise the reference element described above in a conventional electrode containing a reference solution such as a barrel electrode or can be in the form of a dry operative electrode (both as described in *Research Disclosure* 16113, published by Industrial Opportunities Limited, Homewell, Havant, Hampshire, P09, 1EF, UK, Volume 161, September, 1977). Solution assays can be carried out, for example, using barrel type electrodes containing electrode bodies having therein a membrane. The sample is contacted to the membrane and a reference electrode is inserted into the electrode body.

The reference elements described above can be useful in dry operative ion-selective electrodes, which require a membrane layer containing an ionophore.

Dry operative electrodes are those described in U.S. Application Ser. No. 893,656, now U.S. Pat. No. 4,214,968, and comprise a dried reference electrode layer coated with a metal salt layer and a membrane layer.

The membrane of the electrode designed to measure potassium, sodium, $CO_2$, and other ions requiring a membrane can be coated over the reference element by any means, such as roll coating, dip coating and the like.

Among the patents and publications which describe ion-selective membranes of the type useful in the instant invention, the contents of which are incorporated herein by reference to the extent that they are pertinent, are:

U.S. Pat. No. 3,562,129 to Simon, issued Feb. 9, 1971;
U.S. Pat. No. 3,753,887 to Kedem et al, issued Aug. 21, 1973;
U.S. Pat. No. 3,856,649 to Genshaw et al, issued Dec. 24, 1974;
British Pat. No. 1,375,446, issued Nov. 27, 1974;
German OLS No. 2,251,287, issued Apr. 26, 1973;
W. E. Morf, G. Kohr and W. Simon, "Reduction of the Anion Interference in Neutral Carrier Liquid-Membrane Electrodes Responsive to Cations," *Analytical Letters*, Volume 7, No. 1, pages 9 through 22 (1974);
W. E. Morf, D. Ammann, E. Pretsch and W. Simon, "Carrier Antibiotics and Model Compounds as Components of Ion-Sensitive Electrodes," *Pure and Applied Chemistry*, Volume 36, No. 4, pages 421 through 439 (1973);
D. Ammann, E. Pretsch and W. Simon, "Sodium Ion-Selective Electrode Based on a Neutral Carrier," *Analytical Letters*, Volume 7, No. 1, pages 23 through 32 (1974);
R. W. Cattrall and H. Freiser, *Analytical Chemistry*, 43, 1905 (1971); and
H. James, G. Carmack and H. Freiser, *Analytical Chemistry*, 44, 856 (1972).

Membranes of this type are well known. Such membranes generally include an inert hydrophobic binder or matrix having dispersed therein an ion carrier or selector commonly referred to as an ionophore which imparts selectivity to the membrane. These membranes can also contain a carrier solvent for the ionophore to provide adequate ion mobility in the membrane. The carrier solvent generally also serves as a plasticizer for the membrane binder.

The membrane layer generally contains binders, ion carriers, solvents and the like, such as described in the above-noted copending U.S. Application Ser. No. 893,656, filed Apr. 5, 1978.

Figure 2:
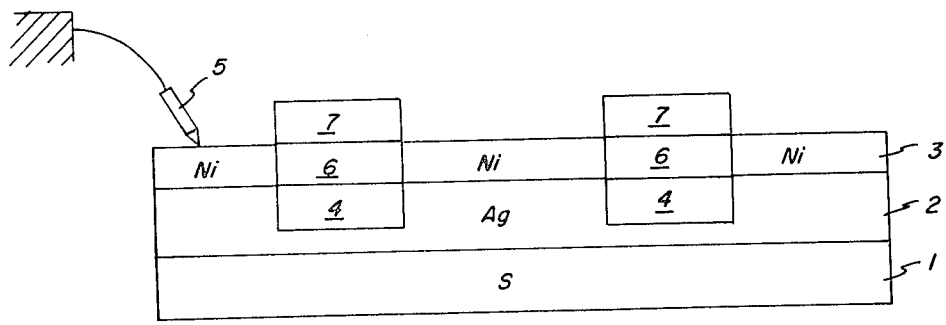
FIG. 2 of the drawings shows a cross-sectional view of an ion-selective membrane electrode as described herein.

The ion-selective electrodes can be manufactured using a conductive wire as the starting material and dipping the wire sequentially into the reference composition and the composition containing the membrane; or a dry operative electrode can be prepared as shown in FIG. 2 by coating, laminating or otherwise applying the individual layers one over another to form a planar, multilayer electrode structure. In FIG. 2, the support 1 is coated with a silver layer 2, stripe coated with nickel, chromium or mixtures or alloys of chromium and nickel 3, and treated with oxidizing agent to form silver halide layer 4 in the unprotected areas. The silver halide layers only are then overcoated with electrolyte layer 6 and membrane layer 7. The probe 5 is contacted with the nickel or chromium layer.

The ion selectivity of membrane electrodes can be observed by measuring a steady-state difference in electrical potential between reference solutions and sample solutions, as described in the above-identified U.S. Application Ser. No. 893,656.

For use as an electrode to detect halide ions such as chloride or bromide ions, the reference electrode can be overcoated with a polymeric layer to reduce any interference from other halide ions, uric acid and the like. Such polymers are described in U.S. Application Ser. No. 956,527 by Battaglia et al filed Oct. 31, 1978, now U.S. Pat. No. 4,199,412. Preferred overcoats include cellulose acetate containing an acetyl content of from 36.5 to 40 weight percent.

The following examples will serve to further demonstrate the successful practice of the present invention.

EXAMPLE 1

A silver film on a poly(ethylene terephthalate) support was prepared by vapor deposition in vacuum. Silver metal was placed in the crucible of an electron beam-heated vapor source and the vacuum chamber was closed and the pressure reduced to $5 \times 10^{-5}$ Torr. The silver was heated in the electron beam of the vapor source to a point where it had melted and was evaporating at a high rate. The support was drawn through the vapor beam at a rate such that the silver that condensed on the support formed a film approximately 2500 Å thick.

Samples of the silver-coated support were attached to masks such that 8 mm wide stripes of the silver film were left exposed. The masked samples were placed in a bell jar vacuum system approximately 15 inches from an electron beam-heated vapor source. Gold splatters were placed in the crucible of the vapor source and the chamber pumped down to a pressure of $\sim 5 \times 10^{-5}$ Torr. The gold was heated to the point of evaporation, the vapor condensing on the exposed areas of the silver film to form a film 500 Å thick.

The pressure in the vacuum system was raised to ambient pressure. The samples were removed and replaced by masked, uncoated samples of silver film. The process was repeated and chromium metal stripes 500 Å thick were deposited on the support instead of gold.

A portion of each striped silver film was bathed in a solution consisting of:

| | | |
|---|---|---|
| Potassium dichromate | 10.1 | g |
| Potassium chloride | 15.4 | g |
| Hydrochloric acid, 6N | 25 | ml |

| | | |
|---|---|---|
| Water to | 1 | liter | for 15 seconds at 23° C. The strips were removed, rinsed with water and dried. In both cases there was no visible reaction with the protective metal stripe or with the underlying silver film. The surface of the unprotected silver film was converted to silver chloride and in the case of the film protected with gold, all of the silver immediately adjacent to the stripes was converted. As a result, electrical continuity was lost between the stripes. The exposed silver on the sample protected with chromium stripes reacted uniformly and the electrical resistance between adjacent stripes was less than 1 ohm.

EXAMPLE 2

A silver film on poly(ethylene terephthalate) support was overcoated with chromium film in a pattern of stripes using the same process described in Example 1. The chromium was deposited at three thicknesses: 260 Å, 140 Å and 60 Å. Samples of all coatings were bathed in the bleach solution of Example 1 as in Example 1 for times ranging from 45 seconds to 180 seconds at 23° C. The films were then rinsed in water and dried.

In each case the unprotected silver appeared to react uniformly with the solution to form silver chloride. Neither the chromium stripes nor the underlying silver reacted with the solution. After removing the silver chloride with ammonia solution, analysis showed that up to 50 percent of the unprotected silver had been converted. No adjacency effects were found and the rate of reaction of the silver with the solution was uniform over the whole area of the exposed silver film. This example further demonstrates that very thin films of chromium (60 Å) are as effective as chromium films 10 times as thick in protecting the silver film.

EXAMPLE 3

A silver film on poly(ethylene terephthalate) support was overcoated with nickel film in a pattern of stripes using the same process described in Example 1. The nickel was deposited in three thicknesses: 265 Å, 130 Å and 53 Å. The samples were bathed in the bleach solution of Examples 1 as in Example 1 for 2 minutes at 23° C. rinsed in water and dried. In each case the unprotected silver appeared to react uniformly with the solution while the nickel stripes and the underlying silver showed no sign of reaction.

The material overcoated with 53 Å of nickel was used to make a series of electroanalytical cells. These were used in an instrument in which the electrical contacts were modified and made smooth so that they did not abrade or pierce the contact area on the cell. In a typical test using standard solutions, voltage measurements on the cells averaged 12.34±0.24 millivolts. In a similar test with sharp, piercing contacts using cells made from materials not having protected contact areas, the average of voltage measurements was 12.94±0.17 millivolts. This example demonstrates that good precision can be obtained using materials that have protected, metallic areas and nonpenetrating electrical contacts. This aids in eliminating the problems that are introduced when sharp, penetrating contacts wear and become less effective.

EXAMPLE 4

A silver film on poly(ethylene terephthalate) support was prepared as described in Example 1. Samples of this silver coating were used to prepare materials with different metal-film protective overcoats which were prepared by the method described in Example 1.

The following coatings were prepared:

| Example | Metal Film Overcoat | Overcoat Thickness (Å) |
|---|---|---|
| 4a | Nickel | 60 |
| 4b | Chromium | 170 |
| Control A | Zinc | 75 |
| Control B | Lead | 60 |
| Control C | Copper | 120 |
| Control D | Aluminum | 120 |
| Control E | Cobalt | 100 |
| Control F | Tin | 130 |

All materials were bathed in the bleach of Example 1 as in Example 1 for 3 minutes at 25° C., rinsed and dried. The nickel and chromium films did not react with the solution and prevented the underlying silver from reacting also. It was found in this case that the rate of reaction of the silver was slightly greater in areas immediately adjacent to the nickel film, but not to the extent that all of the silver layer reacted. Thus, electrical continuity was maintained.

The zinc, lead, copper and aluminum films all reacted with the solution and did not protect the underlying silver from reacting with the solution also. The cobalt film partially protected the silver but in areas where reaction did occur within the cobalt stripe the cobalt was undercut and tended to slough off, exposing silver to the solution.

The tin also afforded a degree of protection to the underlying silver but reacted slowly with the solution to form a salt on its surface. This caused an increase in electrical contact resistance. At the same time, there was a pronounced increase in the rate of reaction of the silver in areas immediately adjacent to the edge of the thin film.

This example illustrates the clear and unusual superiority of nickel and chromium films to other metal films in their ability to protect silver from reaction with corrosive solutions.

EXAMPLE 5

An arrangement for producing striped coatings consisting of an electron beam-heated vapor source, a water-cooled chimney mounted above the source, and a slotted mask and support guide mounted to the top of the chimney at a distance of approximately 24 inches from the vapor source was installed in a coating machine. A roll of poly(ethylene terephthalate), previously coated with silver by the process described in Example 1, was loaded into the machine and threaded through a guide on the stripe mask. The crucible in the vapor source was charged with pure nickel rod. The chamber was closed, pumped down to a pressure $<5\times10^{-5}$ Torr and the nickel was melted in the vapor source. When nickel was evaporating at a high rate and condensing on the silver surface, the support was drawn through the mask at a rate sufficient to cause parallel stripes of nickel film to be deposited on the silver at a thickness of $\sim$130 Å. After the full roll of support was coated, the evaporation was stopped, the chamber pressure raised to ambient pressure and the roll removed. The material was then treated with a solution similar to the formula of Example 1, converting only the surface of the silver in the unprotected areas to silver chloride. The converted areas were subsequently overcoated with a cellulose acetate polymer containing a 36.5 to 40.0 percent acetyl content and the finished material fabricated into slides for measuring chloride ion concentrations in blood serum. Several hundred slides were tested as were an equal number of slides in which the contact area had not been protected using the same analytical instrument. No test failures due to poor contact occurred using the slides with contact areas protected with nickel, while a small but significant number of contact failures occurred with the slides having unprotected contact areas.

The invention has been described in detail with particular reference to preferred embodiments thereof, but it will be understood that variations and modifications can be effected within the spirit and scope of the invention.

What is claimed is:

1. A silver/silver halide electrode comprising a support containing a layer of silver, portions of said layer of silver having thereon a layer of a metal selected from the group consisting of nickel and chromium and mixtures and alloys of nickel and chromium, the portions of silver not covered with metal having thereon a layer of silver halide.

2. The electrode of claim 1 wherein said metal is chromium.

3. The electrode of claim 1 wherein the said metal is nickel.

4. The electrode of claim 1 wherein the metal layer is coated on the silver in stripes.

5. A silver/silver halide reference element comprising a support containing a layer of silver, portions of said layer of silver having thereon a metal selected from the group consisting of nickel and chromium and alloys or mixtures of nickel and chromium, the portions of silver not covered by metal having thereon a first layer of silver halide and a second layer comprising a metal salt.

6. The element of claim 5 wherein the metal layer is coated on said silver layer in stripes.

7. The element of claim 5 wherein the metal salt is selected from the group consisting of halides of ammonium, alkali and alkaline earth metals.

8. The element of claim 5 wherein said metal is chromium.

9. The element of claim 5 wherein said metal is nickel.

10. An ion-selective electrode comprising a support having thereon a silver layer, portions of said silver layer having thereon a metal selected from the group consisting of chromium and nickel and mixtures or alloys of chromium and nickel, the portions of silver not covered with said metal having thereon a first layer of silver halide and a second layer comprising a metal salt and a third layer comprising a membrane comprising an ionophore, a carrier solvent and a hydrophobic binder.

11. The electrode of claim 10 wherein the silver layer is coated with said metal in stripes.

12. The electrode of claim 10 wherein said metal is chromium.

13. The electrode of claim 10 wherein said metal is nickel.

14. The electrode of claim 10 wherein said metal salt layer comprises a hydrophilic binder.

15. The electrode of claim 14 wherein said metal salt is selected from the group consisting of halides of ammonium, alkali metals and alkaline earth metals.

16. The electrode of claim 10 wherein said membrane layer is coated with a polymeric layer.

17. A halide sensitive electrode comprising a silver layer partially coated with chromium or nickel or mixtures or alloys of chromium and nickel and containing silver halide in the uncoated areas of the silver layer wherein the electrode is overcoated with a polymeric layer.

18. The electrode of claim 17 wherein said polymeric layer comprises cellulose acetate.

* * * * *